United States Patent [19]
Otani et al.

[11] Patent Number: 6,090,970
[45] Date of Patent: Jul. 18, 2000

[54] PRODUCTION METHOD OF ALKYLATED CYANOACETYLUREA

[75] Inventors: Yutaka Otani; Hiroki Ueno; Michio Matsuda; Yoshiyuki Imamiya, all of Osaka, Japan

[73] Assignee: Sumika Fine Chemicals Co., Ltd., Osaka, Japan

[21] Appl. No.: 09/321,451

[22] Filed: May 27, 1999

[30] Foreign Application Priority Data

Jun. 19, 1998 [JP] Japan .................................. 10-172483
Sep. 16, 1998 [JP] Japan .................................. 10-261949

[51] Int. Cl.⁷ ................................................. C07C 255/00
[52] U.S. Cl. ............................................................ 558/445
[58] Field of Search ............................................. 558/445

[56] References Cited

U.S. PATENT DOCUMENTS 5,003,099  3/1991  Mettler et al. ........................... 558/445

FOREIGN PATENT DOCUMENTS 0911325  4/1999  European Pat. Off. .

OTHER PUBLICATIONS

Damewood et al., *Journal of Medicinal Chemistry*, vol. 37, No. 20, pp. 3303–3312 (1994).

*Primary Examiner*—Johann Richter
*Assistant Examiner*—Joseph Murray
*Attorney, Agent, or Firm*—Leydig, Voit & Mayer, Ltd.

[57] ABSTRACT

A method for producing alkylated cyanoacetylurea from an easily obtainable starting material. An industrially available cyanoacetylurea and a carbonyl compound are reacted in a polar solvent under reducing conditions to alkylate cyanoacetylurea In addition, a reaction of cyanoacetylurea and acetone under reducing conditions affords isopropylation of cyanoacetylurea.

7 Claims, No Drawings

PRODUCTION METHOD OF ALKYLATED CYANOACETYLUREA

TECHNICAL FIELD OF THE INVENTION

The present invention relates to a production method of an alkylated cyanoacetylamino compound, and to a production method of alkylated cyanoacetylurea which is a useful starting material of a 5-alkyl substituted uracil that is an important intermediate for the production of a pharmaceutical product such as an anti-HIV drug and the like. More particularly, the present invention relates to a production method comprising reacting cyanoacetylurea and a carbonyl compound in a polar solvent under reducing conditions to alkylate cyanoacetylurea. More particularly, the present invention relates to a production method comprising reacting cyanoacetylurea with acetone under reducing conditions to isopropylate the acetyl moiety of cyanoacetylurea.

BACKGROUND OF THE INVENTION

The product of the present invention, alkylated cyanoacetylurea, is a useful starting material of a 5-alkyl substituted uracil which is an important intermediate for producing a pharmaceutical agent (e.g., anti-HIV drug, antiviral agent and the like), agents for photographs (e.g., stabilizer of silver halide and the like), and the like.

As a prior art method for producing alkylated cyanoacetylurea, a method comprising condensing cyanoalkylacetic acid, urea and acetic anhydride by heating is known [*Journal of the American Pharmaceutical Association*, 44, 545 (1955)]. Cyanoalkylacetic acids (starting material) can be obtained by reacting an ester compound of cyanoacetic acid and alkyl halide. However, the reaction requires use of a dangerous reagent (e.g., sodium hydride and the like) in an anhydrous solvent, as well as hydrolysis of ester and subsequent neutralization with an acid for isolation of the product. The inorganic salt (e.g., sodium sulfate and the like) produced at this stage contaminates tools and the like used for the reaction and this method is disadvantageous for the production at a plant scale.

What is more, alkylated cyanoacetylurea cannot be obtained at a high yield by a production method comprising direct alkylation of cyanoacetylurea.

There is therefore a demand for an easy, convenient and industrially-utilizable method for producing alkylated cyanoacetylurea from a starting material that is easily obtainable.

It is therefore an object of the present invention to provide a method for an easy, convenient and industrially-utilizable method for producing alkylated cyanoacetylurea useful as a synthetic starting material of 5-alkyl substituted uracils from a starting material that is easily obtainable. Another object of the present invention is to provide a method for an easy, convenient and industrially-utilizable method for producing an alkylated cyanoacetylamino compound.

SUMMARY OF THE INVENTION

Such object can be achieved by the following method of the present invention, comprising reacting an industrially available cyanoacetylamino compound and a carbonyl compound in a polar solvent under reducing conditions to alkylate the cyanoacetylamino compound, and a method comprising reacting cyanoacetylurea and a carbonyl compound in a polar solvent under reducing conditions, whereby cyanoacetylurea can be alkylated. It has been also found that by reacting cyanoacetylurea with acetone as a solvent and reagent under reducing conditions, the acetyl moiety of cyanoacetylurea can be converted to isopropyl.

Accordingly, the present invention provides the following.

(1) A method for producing a cyanoacetylamino compound having a group of the formula

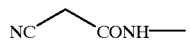

an acetyl moiety thereof is alkylated with an optionally substituted alkyl, comprising reacting a cyanoacetylamino compound having a group of the formula

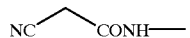

a carbonyl compound in a polar solvent under reducing conditions.

(2) The production method of (1) above, wherein the reaction proceeds in the presence of a reduction catalyst.

(3) The production method of (1) above, wherein the cyanoacetylamino compound is cyanoacetylurea.

(4) The production method of (2) above, wherein the cyanoacetylamino compound is cyanoacetylurea.

(5) A method for producing an alkylated cyanoacetylurea of the formula (c)

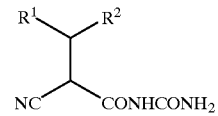

wherein $R^1$ and $R^2$ may be the same or different and each is a hydrogen atom, an alkyl having 1 to 12 carbon atoms, a cyclic alkyl having 3 to 8 carbon atoms, an aromatic ring or an aralkyl, comprising reacting cyanoacetylurea of the formula (a)

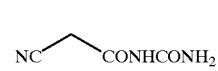

and a carbonyl compound of the formula (b)

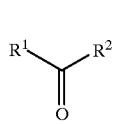

wherein $R^1$ and $R^2$ are as defined above, in a polar solvent under reducing conditions.

(6) A method for producing N-(2-cyano-3-methylbutanoyl)urea, comprising reacting cyanoacetylurea of the formula (a)

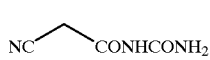

(a)

with acetone under reducing conditions.

(7) The production method of (6) above, wherein the reaction is carried out in the presence of a reduction catalyst.

DETAILED DESCRIPTION OF THE INVENTION

Each symbol used in the present specification is explained in the following.

The alkyl having 1 to 12 carbon atoms at $R^1$ and $R^2$ may be linear or branched and is exemplified by methyl, ethyl, propyl, isopropyl, butyl, isobutyl, tert-butyl, pentyl, hexyl, heptyl, octyl, nonyl, decyl, undecyl, dodecyl and the like. Preferred is alkyl having 1 to 6 carbon atoms, such as methyl, ethyl, propyl, isopropyl, butyl, isobutyl, tert-butyl, pentyl, hexyl and the like.

The cyclic alkyl having 3 to 8 carbon atoms at $R^1$ and $R^2$ may be, for example, cyclopropyl, cyclobutyl, cyclopentyl, cyclohexyl, cycloheptyl, cyclooctyl and the like, with preference given to cyclohexyl.

The aromatic ring at $R^1$ and $R^2$ may be, for example, phenyl, pyridyl and the like, with preference given to phenyl.

The aralkyl at $R^1$ and $R^2$ may be, for example, that wherein the alkyl moiety has 1 or 2 carbon atoms, such as benzyl, phenylethyl and the like.

In the present invention, the optionally substituted alkyl is an alkyl having 1 to 25, preferably 1 to 3, carbon atoms, which is optionally substituted by 1 to 3 substituent(s) selected from $C_3$–$C_8$ cyclic alkyl, aromatic ring and aralkyl. As used herein, $C_3$–$C_8$ cyclic alkyl, aromatic ring and aralkyl are as defined for the above-mentioned $R^1$ and $R^2$.

Examples of the carbonyl compound include formaldehyde, acetone, methyl ethyl ketone, methyl isobutyl ketone, diethyl ketone, cyclopropyl methyl ketone, acetophenone, acetaldehyde, propionaldehyde, cyclohexanecarbaldehyde, benzaldehyde, 3-pyridinecarbaldehyde, phenylacetaldehyde and the like.

The carbonyl compound (starting material) may be commercially available or one synthesized by the method disclosed in, for example, *Organic Reactions*, Vol. VI, 207 and *Journal Organic Chemistry*, 52, 2559 (1987).

The production method of the present invention using a polar solvent is explained in the following by referring to the alkylation of cyanoacetylurea as an example. Other compounds can be also produced in a similar manner.

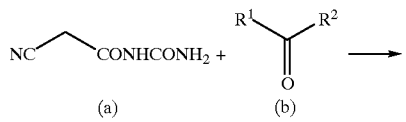

-continued

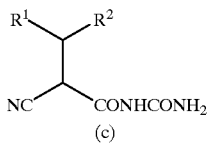

(c)

wherein $R^1$ and $R^2$ are as defined above.

The cyanoacetylurea of the formula (a) is suspended or dissolved in a polar solvent, and a carbonyl compound of the formula (b), acetic acid and ammonium acetate are added to allow reaction under reducing conditions to give cyanoacetylurea of the formula (c), that has been alkylated with an optionally substituted alkyl. Preferably, the reaction is carried out in the presence of a reduction catalyst. The termination of the reaction is confirmed by the disappearance or decrease of the starting material, which is known by way of high performance liquid chromatography. After reaction, the objective product is isolated by any method which is free of any limitation. For example, the catalyst is filtered off and water is added to the filtrate or the filtrate is cooled to precipitate and isolate the objective product.

In the same manner as above, a compound having cyanoacetylamino group is reacted with a carbonyl compound to give a compound having a cyanoacetylamino group, wherein the acetyl moiety is alkylated with an optionally substituted alkyl.

While the reaction time varies depending on the amount of catalyst, it is generally 3 to 12 hours and the reaction temperature is from 0° C. to 50° C., preferably from 20° C. to 30° C. The hydrogen pressure is from under normal pressure to 30 kg/cm², preferably from under normal pressure to 15 kg/cm².

The carbonyl compound, which is the starting material, is added in a 1.0-fold to 2.0-fold amount, preferably 1.1-fold to 1.5-fold amount, per mole of cyanoacetylurea.

Acetic acid is added in a 0.1-fold to 1.0-fold amount, preferably 0.2-fold to 0.4-fold amount, per mole of cyanoacetylurea.

Ammonium acetate is added in a 0.05-fold to 0.5-fold amount, preferably 0.1-fold to 0.2-fold amount, per mole of cyanoacetylurea.

The reduction catalyst may be one typically used for reductive alkylation, which is preferably palladium carbon, platinum carbon and the like.

The reduction catalyst is used in a proportion of 0.5–30 wt %, preferably 1–10 wt %, relative to cyanoacetylurea, when, for example, 10% palladium carbon (50% wet product) is used.

The polar solvent to be used for the reaction has a relative dielectric constant of not less than 10.

Examples of the reaction solvent include linear or branched lower alcohols having 1 to 4 carbon atoms (e.g., methanol, ethanol, propanol, isopropanol, butanol and tert-butanol), polar organic solvent (e.g., N,N-dimethylformamide, N,N-dimethylacetamide, dimethyl sulfoxide and the like), glycols [e.g., ethylene glycol, ethylene glycol monomethyl ether (trademark: methyl cellosolve) and the like], water and mixed solvents thereof. Preferred are isopropanol and N,N-dimethylformamide. When the carbonyl compound to be used as a reaction reagent can be used as a polar solvent, this carbonyl compound may be used as a reaction solvent.

The reaction solvent is used in a 1-fold to 10-fold weight amount relative to cyanoacetylurea.

The acetyl moiety of cyanoacetylurea can be converted to isopropyl according to the above-mentioned production method. Acetone (formula (b) wherein $R^1$ and $R^2$ are methyl) to be used as a reaction reagent can be also used as a reaction solvent for the reaction.

When acetone is used as a reaction solvent, the production method is almost the same as the one mentioned above, wherein cyanoacetylurea is suspended or dissolved in acetone, and acetic acid and ammonium acetate are added to allow reaction under reducing conditions to give N-(2-cyano-3-methylbutanoyl)urea. Preferably, the reaction is carried out in the presence of a reduction catalyst. The termination of the reaction can be confirmed and the objective product can be isolated after the reaction, according to the above-mentioned methods.

While the reaction time varies depending on the amount of catalyst, it is preferably 3 to 12 hours and the reaction temperature is from 0° C. to 50° C., preferably from 30° C. to 40° C. The hydrogen pressure is from normal pressure to 30 kg/cm$^2$, preferably from normal pressure to 10 kg/cm$^2$.

In the method using acetone as a reaction solvent, acetone is used as a solvent and reaction reagent. The amount of acetone as a reaction reagent is 1.0-fold to 2.0-fold molar amount, preferably 1.1-fold to 1.5-fold molar amount, per mole of cyanoacetylurea, and the amount of acetone as a solvent is 1-fold to 20-fold weight amount, preferably 5-fold to 10-fold weight amount, relative to cyanoacetylurea.

In the method using acetone as a reaction solvent, the amount of acetic acid to be used is 0.1-fold to 1.0-fold molar amount, preferably 0.2-fold to 0.4-fold molar amount, per mole of cyanoacetylurea.

In the method using acetone as a reaction solvent, the amount of ammonium acetate to be used is 0.05-fold to 0.5-fold molar amount, preferably 0.1-fold to 0.2-fold molar amount, per mole of cyanoacetylurea.

The reduction catalyst is generally one used for reductive alkylation, which is preferably palladium carbon, platinum carbon and the like.

The reduction catalyst is used in a proportion of 0.5–30 wt %, preferably 1–10 wt %, relative to cyanoacetylurea, when, for example, 5% palladium carbon (50% wet product) is used.

The present invention is explained in detail by illustrative examples, to which the present invention is not limited in any way.

EXAMPLE 1

Cyanoacetylurea (38.7 g) was suspended in N,N-dimethylformamide (77.4 ml), and acetone (24.6 ml), acetic acid (3.43 ml) and ammonium acetate (2.31 g) were added. This suspension was subjected to catalytic hydrogenation in the presence of 10% palladium carbon (0.78 g, 50% wet product) under normal pressure at 30° C. for 9 hours. The reaction mixture was heated to 70° C., and the catalyst was filtered off. Water (150 ml) was added to the filtrate to allow precipitation of crystals. The crystals were collected by filtration to give N-(2-cyano-3-methylbutanoyl)urea (yield 40.1 g).

Melting point: 173–174° C. IR(Nujol):3336,2256,1690, 1106 cm$^{-1}$ $^1$H-NMR(270 MHz, DMSO-d$_6$)δ 0.97(3H, d), 1.00(3H,d), 2.15–2.35(1H,m), 3.85(1H,d), 7.44(2H, br), 10.49(1H,br)

EXAMPLE 2

Cyanoacetylurea (116.1 g) was suspended in N,N-dimethylformamide (219.3 ml), and acetone (73.1 ml), acetic acid (10.8 ml) and ammonium acetate (6.93 g) were added. This suspension was subjected to catalytic hydrogenation in the presence of 10% palladium carbon (2.33 g, 50% wet product) under hydrogen pressure at 10 kg/cm$^2$ and at 25° C. for 4 hours. The reaction mixture was heated to 70° C., and the catalyst was filtered off. Water (745 ml) was added to the filtrate to allow precipitation of crystals. The crystals were collected by filtration to give crystals of N-(2-cyano-3-methylbutanoyl)urea (yield 134.5 g).

The data of the obtained compound were as those obtained in Example 1.

EXAMPLE 3

Cyanoacetylurea (38.7 g) was suspended in isopropanol (77.4 ml), and acetone (24.6 ml), acetic acid (3.43 ml) and ammonium acetate (2.31 g) were added. This suspension was subjected to catalytic hydrogenation in the presence of 10% palladium carbon (0.78 g, 50% wet product) under normal pressure at 30° C. for 8 hours. The reaction mixture was heated to 80° C. for 1 hour, and the catalyst was filtered off. Water (150 ml) was added to the filtrate to allow precipitation of crystals. The crystals were collected by filtration to give crystals of N-(2-cyano-3-methylbutanoyl)urea (yield 21.7 g).

The data of the obtained compound were as those obtained in Example 1.

EXAMPLE 4

Cyanoacetylurea (38.7 g) was suspended in N,N-dimethylformamide (77.4 ml), and acetaldehyde (18.8 ml), acetic acid (3.43 ml) and ammonium acetate (2.31 g) were added. This suspension was subjected to catalytic hydrogenation in the presence of 10% palladium carbon (0.78 g, 50% wet product) under normal pressure at 30° C. for 5 hours. The catalyst was filtered off. Water (350 ml) was added to the filtrate to allow precipitation of crystals. The crystals were collected by filtration to give crystals of N-(2-cyanobutanoyl)urea (yield 24.2 g). $^1$H-NMR(270 MHz, DMSO-d$_6$)δ 0.99(3H,t), 1.75–1.95(2H,m), 3.86(1H, t), 7.42(2H,br), 10.50(1H,br)

EXAMPLE 5

Cyanoacetylurea (78.6 g) was suspended in N,N-dimethylformamide (154.9 ml), and acetone (48.8 g), acetic acid (7.2 g) and ammonium acetate (4.6 g) were added. This suspension was subjected to catalytic hydrogenation in the presence of 10% palladium carbon (3.1 g, 50% wet product) under hydrogen pressure at 10 kg/cm$^2$ and at 25° C. for 4 hours. The reaction mixture was heated to 70° C. to dissolve an insoluble matter, and the catalyst was filtered off. Water (390 ml) was added to the obtained filtrate to allow precipitation of crystals. The crystals were collected by filtration to give crystals of N-(2-cyano-3-methylbutanoyl)urea (yield 89.7 g).

The data of the obtained compound were as those obtained in Example 1.

EXAMPLE 6

Cyanoacetylurea (51.6 g) was suspended in acetone (516 ml), and acetic acid (4.8 g) and ammonium acetate (3.2 g) were added. This suspension was subjected to catalytic hydrogenation in the presence of 5% palladium carbon (4.1 g, 50% wet product) under normal pressure at 40° C. for 5 hours. The reaction mixture was refluxed under heating to dissolve an insoluble matter, and the catalyst was filtered off. The obtained filtrate was concentrated to a half, and water (258 ml) was added to the filtrate to allow precipitation of crystals. The crystals were collected by filtration to give crystals of N-(2-cyano-3-methylbutanoyl)urea (yield 62.5 g).

Melting point: 173–174° C. IR(Nujol):3336,2256,1690, 1106 cm$^{-1}$ $^1$H-NMR(270 MHz, DMSO-d$_6$) 0.96(3H,d), 1.00(3H,d), 2.15–2.35(1H,m), 3.85(1H,d), 7.44(2H, br), 10.49(1H,br)

EXAMPLE 7

Cyanoacetylurea (25.8 g) was suspended in acetone (258 ml), and acetic acid (2.4 g) and ammonium acetate (1.5 g) were added. This suspension was subjected to catalytic hydrogenation in the presence of 5% palladium carbon (2.1 g, 50% wet product) under hydrogen pressure at 10 kg/cm$^2$ and at 40° C. for 1 hour. The reaction mixture was refluxed under heating to dissolve an insoluble matter, and the catalyst was filtered off. The obtained filtrate was concentrated to a half. Water (130 ml) was added to the filtrate to allow precipitation of crystals. The crystals were collected by filtration to give crystals of N-(2-cyano-3-methylbutanoyl)urea (yield 30.7 g).

The data of the obtained compound were as those obtained in Example 6.

According to the present invention, industrially available cyanoacetylurea can be alkylated by an easy, convenient and industrially-utilizable method, whereby a useful starting material of a 5-alkyl substituted uracil which is an important intermediate for producing pharmaceutical agents (e.g., anti-HIV drug, antiviral drug and the like), agents for photographs (e.g., stabilizer of silver halide and the like), and the like can be provided. Further, the present invention enables alkylation of acetyl moiety of the compound having cyanoacetylamino group, according to the easy, convenient and industrially-utilizable method.

This application is based on patent application Nos. 172483/1998 and 261949/1998 filed in Japan, the contents of which are hereby incorporated by reference.

What is claimed is:

1. A method for producing a cyanoacetylamino compound having a group of the formula

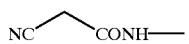

an acetyl moiety thereof is alkylated with an optionally substituted alkyl, comprising reacting a cyanoacetylamino compound having a group of the formula

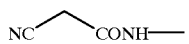

a carbonyl compound in a polar solvent under reducing conditions.

2. The production method of claim 1, wherein the reaction proceeds in the presence of a reduction catalyst.

3. The production method of claim 1, wherein the cyanoacetylamino compound is cyanoacetylurea.

4. The production method of claim 2, wherein the cyanoacetylamino compound is cyanoacetylurea.

5. A method for producing an alkylated cyanoacetylurea of the formula (c)

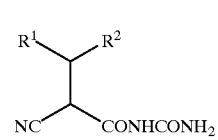

wherein R$^1$ and R$^2$ are the same or different and each is a hydrogen atom, an alkyl having 1 to 12 carbon atoms, a cyclic alkyl having 3 to 8 carbon atoms, an aromatic ring or an aralkyl, comprising reacting cyanoacetylurea of the formula (a)

and a carbonyl compound of the formula (b)

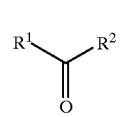

wherein R$^1$ and R$^2$ are as defined above, in a polar solvent under reducing conditions.

6. A method for producing N-(2-cyano-3-methylbutanoyl)urea, comprising reacting cyanoacetylurea of the formula (a)

with acetone under reducing conditions.

7. The production method of claim 6, wherein the reaction is carried out in the presence of a reduction catalyst.

* * * * *

UNITED STATES PATENT AND TRADEMARK OFFICE
CERTIFICATE OF CORRECTION

PATENT NO. : 6,090,970
DATED : July 18, 2000
INVENTOR(S) : Otani et al.

Page 1 of 1

It is certified that error appears in the above-identified patent and that said Letters Patent is hereby corrected as shown below:

<u>Claim 1, Column 7,</u>
Line 45, "an acetyl moiety thereof is alkylated with an optionally" should read -- wherein an acetyl moiety thereof is alkylated with an optionally --.
Line 53, "a carbonyl compound in a polar solvent under reducing" should read -- and a carbonyl compound in a polar solvent under reducing --.

Signed and Sealed this

Eighteenth Day of September, 2001

Attest:

*Nicholas P. Godici*

NICHOLAS P. GODICI
*Attesting Officer*    *Acting Director of the United States Patent and Trademark Office*